United States Patent
Lüchinger

(10) Patent No.: US 8,176,950 B2
(45) Date of Patent: May 15, 2012

(54) DOSAGE-DISPENSING DEVICE WITH A CHANGING MECHANISM FOR DOSAGE-DISPENSING UNITS

(75) Inventor: Paul Lüchinger, Uster (CH)

(73) Assignee: Mettler-Toledo AG, Greifensee (CH)

( * ) Notice: Subject to any disclaimer, the term of this patent is extended or adjusted under 35 U.S.C. 154(b) by 0 days.

(21) Appl. No.: 13/101,184

(22) Filed: May 5, 2011

(65) Prior Publication Data

US 2011/0204088 A1     Aug. 25, 2011

Related U.S. Application Data

(63) Continuation of application No. PCT/EP2009/061987, filed on Sep. 16, 2009.

(30) Foreign Application Priority Data

Nov. 10, 2008  (EP) ..................................... 08168761

(51) Int. Cl.
    *B65B 3/04*      (2006.01)
    *B65B 1/04*      (2006.01)

(52) U.S. Cl. .......... 141/83; 141/104; 141/251; 141/284; 141/371

(58) Field of Classification Search ..................... 141/83, 141/100, 104, 250–259, 284, 369–373
See application file for complete search history.

(56) References Cited

U.S. PATENT DOCUMENTS

| | | | |
|---|---|---|---|
| 3,878,907 A * | 4/1975 | Morick ............................ | 141/83 |
| 4,335,759 A * | 6/1982 | Pattiniemi et al. ................ | 141/5 |
| 4,544,279 A * | 10/1985 | Rudolph ............................ | 222/1 |
| 4,628,974 A * | 12/1986 | Meyer ............................ | 141/129 |
| 4,867,258 A * | 9/1989 | Narukawa et al. ............... | 141/83 |
| 4,967,938 A * | 11/1990 | Hellenberg ..................... | 141/104 |
| 5,038,839 A * | 8/1991 | Morimoto et al. ............... | 141/83 |
| 5,078,302 A * | 1/1992 | Hellenberg ..................... | 141/104 |
| 5,950,874 A * | 9/1999 | Sindoni ......................... | 141/104 |
| 6,202,895 B1 * | 3/2001 | Fox ............................... | 141/104 |
| 6,615,881 B2 * | 9/2003 | Bartholomew et al. ......... | 141/18 |
| 6,805,175 B1 * | 10/2004 | Pinkas et al. ................... | 141/130 |
| 7,082,970 B2 * | 8/2006 | Bartholomew et al. ........ | 141/104 |
| 7,134,459 B2 * | 11/2006 | Carlson et al. ................. | 141/130 |
| 7,134,573 B2 * | 11/2006 | Post ................................ | 222/1 |
| 7,347,344 B2 * | 3/2008 | Engels et al. .................. | 222/144 |
| 7,360,564 B2 * | 4/2008 | Engels et al. ................... | 141/83 |
| 7,475,710 B2 * | 1/2009 | Bartholomew et al. ........ | 141/104 |

(Continued)

FOREIGN PATENT DOCUMENTS

DE          19841478 A1       3/1999

*Primary Examiner* — Gregory Huson
*Assistant Examiner* — Nicolas A Arnett
(74) *Attorney, Agent, or Firm* — Standley Law Group LLP

(57) ABSTRACT

A device for dispensing a dosage includes a base frame, at least one device for receiving any dosage-dispensing unit or functional unit that is compatible to be inserted therein, a holder and at least one drive mechanism. The holder has at least one holding position for a dosage-dispensing unit or functional unit. A weighing cell arranged on a lower horizontal plane of the base frame includes a load receiver to receive a target container. A changing mechanism enables the receiving device to be moved horizontally relative to the base frame. This horizontal shift allows a dosage-dispensing unit or functional unit to be interchanged between the holding position and the receiving device. The changing mechanism also permits the receiving device, together with the drive mechanism, to be moved vertically with regard to the base frame.

21 Claims, 6 Drawing Sheets

U.S. PATENT DOCUMENTS

| | | | |
|---|---|---|---|
| 7,527,078 B2 * | 5/2009 | Driessen et al. | 141/9 |
| 7,614,429 B2 * | 11/2009 | Pluvinage et al. | 141/5 |
| 7,690,405 B2 * | 4/2010 | Miller et al. | 141/104 |
| 7,789,111 B2 * | 9/2010 | Luehrsen et al. | 141/83 |
| 8,011,394 B2 * | 9/2011 | Luehrsen et al. | 141/83 |
| 2008/0072993 A1 * | 3/2008 | Luchinger et al. | 141/18 |
| 2008/0173668 A1 | 7/2008 | Bloechlinger et al. | |
| 2008/0190513 A1 | 8/2008 | Luechinger et al. | |
| 2008/0190518 A1 | 8/2008 | Luechinger et al. | |
| 2010/0051648 A1 | 3/2010 | Lüchinger et al. | |

* cited by examiner

DOSAGE-DISPENSING DEVICE WITH A CHANGING MECHANISM FOR DOSAGE-DISPENSING UNITS

CROSS-REFERENCE TO RELATED TO APPLICATIONS

This application is a continuation under 35 USC §120 of PCT/EP2009/061987, filed 16 Sep. 2009, which is in turn entitled to benefit of a right of priority under 35 USC §119 from European patent application 08 16 8761.8, which was filed 10 Nov. 2008. The content of each of the applications is incorporated by reference as if fully recited herein.

TECHNICAL FIELD

The present invention concerns a dosage-dispensing device with a changing mechanism for dosage-dispensing units or functional units.

BACKGROUND

Dosage-dispensing devices for dosage material in the form of a powder or paste are used in particular to dispense small dosage quantities with high precision into small target containers. Such target containers are often placed on a balance in order to weigh the substance delivered out of the dosage-dispensing device, so that the substance can subsequently be processed further in accordance with given instructions. The dosage material is for example contained in a dosage-dispensing unit which includes in essence a source container and a dispensing head. Arranged in the dispensing head is a flow-regulating element, for example a slider gate, which upon actuation opens an outlet orifice. Passing through the outlet orifice which is connected to the source container, the dosage material can then flow into a target container which is arranged below the outlet orifice. The slider gate is preferably designed so that it can be coupled to a drive mechanism that is separate from the dosage-dispensing unit.

Dosage-dispensing devices of this kind are also often used to prepare mixtures of several individual substances. For this purpose, there is preferably a changing mechanism available whereby the individual dosage-dispensing units with the individual substances can automatically be set into, and taken out of, the dosage-dispensing device.

A dosage-dispensing device is disclosed in EP 1 947 427 A1 in which several dosage-dispensing units are arranged in a holder. The dosage-dispensing unit can be transferred between the holder and the receiving location of the dosage-dispensing device by means of a loading mechanism, for example an industrial robot. This solution has a serious disadvantage in that the entire system with its arrangement of individual separate modules requires a large surface area to set up, i.e. it has a large footprint. In laboratory facilities, especially in work compartments with exhaust systems, the footprint of any piece of equipment used inside the compartment is a central issue, as there are many of these compartments installed at users' facilities and space limitations are therefore a real concern. Furthermore, when such a comprehensive setup is installed, one has to anticipate a major project for the adjusting, cabling and programming between the dosage-dispensing device, the loading mechanism and the holder.

These disadvantages are in part countered by two versions of a dosage-dispensing device with a changing mechanism which are disclosed in EP 1 959 244 A1. In the first version, a holder for several dosage-dispensing units is movable along a linear path. The second version has a ring-shaped holder which is arranged so that it surrounds the dosage-dispensing device and can turn around the latter. Depending on the selection, for example based on a formula that is preset in the dosage-dispensing device, the individual dosage-dispensing units are moved into place one after another in accordance with their position number, they are coupled to the drive mechanism, and the substance quantities prescribed in the formula are dispensed into a target container. However, this arrangement still takes up a relatively large surface area as the changing mechanism is arranged at only a small height above the work surface, and the surface space below the changing mechanism can therefore not be utilized.

The different versions of a dosage-dispensing device with a changing mechanism according to the foregoing description are easy to produce, take up little surface space and, due to the fact that the changing mechanism device is incorporated in the device, can be put into operation without a major installation effort.

As an additional requirement however, in order to avoid contamination of the surrounding space and of the substance itself, the distance from the outlet orifice of a dosage-dispensing unit to the fill opening of a target container set on the weighing pan of the weighing cell should be as small as possible. This is of particular importance in the handling of toxic or highly reactive substances. It is preferable if a part of the dosage-dispensing unit that includes the outlet orifice at its lower end actually reaches inside the fill opening during the dispensing process, so that the area inside the rim of the target container is not contaminated with dosage material. This is not possible with the dosage-dispensing devices disclosed in EP 1 959 244 A1. To provide this capability, the entire changing mechanism would have to be height-adjustable. Consequently, the combined weight of all of the dosage-dispensing units that can be set into the changing mechanism would have to be moved vertically up and down. The large mass that would have to be moved could affect the speed of the individual steps in the changing of the dosage-dispensing units and could lead to increased vibrations. Furthermore, the entire space within which the changing mechanism can move needs to be kept free of other objects and other parts of the apparatus. Also, the holder cannot be moved during the dosage-dispensing process.

It is therefore the object to create a dosage-dispensing device whose requirements for surface area and for clear air space are small and which allows a fast change and a rapid loading of dosage-dispensing units or functional units.

SUMMARY

This task is solved with a dosage-dispensing device that includes a change mechanism and has the features specified in the independent patent claim.

A dosage-dispensing device includes a base frame, at least one receiving device to receive any dosage-dispensing unit or functional unit that is compatible to be inserted in the receiving device, and at least one drive mechanism. After a dosage-dispensing unit or functional unit has been inserted into the receiving device, it can be coupled to the drive mechanism. A holder is arranged, relative to the operating position of the dosage-dispensing device, on an upper horizontal plane of the base frame and connected to the latter. The holder has at least one holding position for a dosage-dispensing unit or functional unit. Further, on a lower horizontal plane of the base frame, there is a weighing cell arranged which includes a load receiver to receive a target container.

In the disclosed embodiments, the dosage-dispensing device includes a changing mechanism which enables the receiving device to be moved horizontally relative to the base frame. With the horizontal position shift, the receiving device allows a dosage-dispensing unit or functional unit to be taken out of its holding position and received into the receiving device and conversely, to be taken out of the receiving device and received into the holding position. Furthermore, by means of the changing mechanism, the receiving device together with the drive mechanism can be moved vertically relative to the base frame in the direction towards the fill opening of a target container that has been set on the load receiver, as well as in the direction away from the fill opening of a target container, i.e. towards the holding position.

The structure and function of a dosage-dispensing unit have been explained and described already in the preceding account of the state of the art. Obviously, instead of one or more dosage-dispensing units, it is also possible to use functional units performing different functions. The concept of such functional units which can be set into a dosage-dispensing device is presented in detail in European Patent Application EP 1 959 243 A1, whose entire content is hereby incorporated by reference. Especially worth mentioning are functional units which are supplied from the outside, for example a pump unit or valve unit which, by means of a supply conduit, are connected to an external reservoir containing a liquid or a gas. This allows the functional unit to be supplied continuously with a free-flowing medium.

Accordingly, the changing mechanism has at least one horizontal linear guide as a connecting element between the receiving device and the driving mechanism, and a vertical linear guide connecting the unit consisting of driving mechanism and receiving device with the base frame. In addition, there is a drive unit for each linear guide, with a controller to direct the drive units. As described above, the horizontal movements serve primarily to transfer the dosage-dispensing unit or functional unit between the receiving device and the holding position. However, this does not exclude the possibility to also use the horizontal movement for necessary functions of a secondary nature such as for example to align the dosage-dispensing unit or functional unit with the target container. The vertical movements serve primarily to transport the dosage-dispensing unit or functional unit from the holding position to the target container and vice versa. Analogous to the horizontal movement, this also does not exclude the possibility to use the vertical movement for other necessary functions, for example short up or down movements to secure and release a locking device.

The holder preferably has at least two holding positions and is designed for linear movement or rotary movement relative to the base frame. Ideally, the location of each holding position is stored in an electronic memory unit of the dosage-dispensing device, so that an operating program which can be executed in a processor module of the dosage-dispensing device can find the desired holding position and turn the latter to a transfer location that will be described hereinafter. Of course, the electronic memory unit can also be used to store data of the dosage-dispensing unit which is seated at the holding position. If there is an electronic reader device, for example an RFID reader, arranged in the area of the holder and if the dosage-dispensing unit has an identifier element, for example an RFID tag, the data of each dosage-dispensing unit or functional unit can also be registered automatically at the time the holder is being populated with dosage-dispensing units. Such data can include the technical data of the dosage-dispensing unit such as for example the date it was put into service, the number of dosage-dispensing cycles, the date of the last dosage-dispensing operation, and similar information. Further data can relate to the substance contained in the dosage-dispensing unit, for example the type and composition of the substance, its expiration date, measured parameters regarding its flow properties and the like. The functional units can likewise have an RFID memory chip on which technical data regarding their function are stored. Possibly, this memory chip may also contain operating information or even program modules that can be retrieved, which serve to influence and/or control individual process steps of the dosage-dispensing device. The ability of the holder to move independently is particularly advantageous for the data acquisition and for loading the apparatus with dosage-dispensing units or functional units. Thus, the holder can be loaded from a single direction even during a dosage-dispensing process, and only one read/write device is needed to register the data of all RFID storage chips. Furthermore, as soon as the receiving device has left the upper plane, each of the dosage-dispensing units or functional units that are present in the holder can at any time be moved past the read/write device to have its data scanned or changed.

The at least one holding position preferably has at least two holder grooves, and the receiving device comprises at least two supports. Furthermore, seating locations which are matched to the supports and guide tracks which are matched to the holder grooves are formed on the dosage-dispensing unit or functional unit. The holder grooves, seating locations, supports and guide tracks are preferably oriented parallel to each other in their lengthwise direction as well as parallel to the horizontal movement of the changing mechanism.

To allow an extraordinarily compact configuration of the dosage-dispensing unit, the functional unit, the holding position and the receiving device, the supports of the receiving device preferably reach into the holding position. This becomes possible if the dosage-dispensing unit or functional unit is arranged between a vertically oriented inner and outer pair of planes, wherein each plane of the inner pair of planes contains at least one seating location and each plane of the outer pair of planes contains at least one guide track.

The loading of the at least holding position with a dosage-dispensing unit can be performed manually. However, if the dosage-dispensing device is, for example, incorporated in a larger system, it may suggest itself to perform the loading of the holding position or the holder by means of a loading mechanism. To satisfy this purpose, there is at least one coupling location for a gripper formed on the dosage-dispensing unit or functional unit. The loading mechanism, for example an industrial robot, has a gripper which can enter into engagement with the coupling location, so that the dosage-dispensing unit or functional unit can be connected to the loading mechanism through a contact-force engagement or a form-fitting engagement. In order to avoid the propagation of shocks and vibrations, it is preferred to arrange the loading mechanism to be independent of the dosage-dispensing device. It is practical if the loading of the holding position with a dosage-dispensing unit or functional unit is performed by means of a horizontal movement that is directed towards the base frame, since no components of the dosage-dispensing device obstruct a movement in this direction. Of course, the holding position and specifically the holder grooves need to be configured in such a way that the loading from this direction, from "in front" so to speak, is possible. Ideally, the changing mechanism likewise moves the dosage-dispensing unit or functional unit from this direction into the at least one holding position, in order to remove the dosage-dispensing unit or functional unit from the receiving device. Accordingly, the transfer of the dosage-dispensing device into the receiving device occurs in a horizontal movement that is directed away from the base frame. Particularly in the loading process, the freedom of the holder to move independently of the receiving device is very advantageous. This makes it possible to load the holder from a single direction even during dosage-dispensing operations.

To prevent the dosage-dispensing unit or functional unit from falling out of the receiving device during transfer movements or from falling out of the holding position as a result of mechanical shocks or disturbances, a snap-lock element which is releasable by a mechanical force can be arranged between at least one holder groove and a guide track and/or between at least one support and a seating location. Such snap-lock elements can be spring-biased ball-catch elements, spring-biased tongues and the like, or even magnet pairs.

Instead of a snap-lock element, the at least one holder groove and/or seating location can have a recess extending essentially in the vertical direction and orthogonal to the longitudinal axis of the holder groove or seating location, while on the at least one guide track and/or on the support a projection is formed which extends essentially in the vertical direction and orthogonal to the longitudinal axis of the guide track or the support. A vertical unlocking movement will be necessary in this case in order to separate the dosage-dispensing device from the receiving device and/or from the at least one holding position. Conversely, a vertical set-down movement is required to set the dosage-dispensing unit or functional unit into the receiving device and/or into the at least holding position.

Depending on the field of use, for example in development laboratories for pharmaceutical substances, the ability is required to dispense minute quantities of these substances with high precision. Dosage-dispensing devices meeting these requirements have a high-precision weighing cell whose signal is used to monitor and control the dosage-dispensing process. The dispensing and measuring process therefore takes place inside a draft shield, so that air turbulence of the ambient environment does not affect the weighing result. In order to avoid complicated designs of draft shields with mechanically challenging air locks, the changing mechanisms disclosed in EP 1 959 244 A1 would have to be arranged inside the draft shield. However, the larger the size of the draft shield, the longer it takes for air turbulences, which may be caused for example by an exchange of a dosage-dispensing unit inside the draft shield, to come to rest. Further, with a larger interior volume of the draft shield, there is an increased likelihood that temperature differences inside the weighing compartment will give rise to air movements. This has the consequence that the interior volume of the draft shield also determines to a significant extent how narrow the tolerance can be set for the given mass target.

The dosage-dispensing device with a changing mechanism as disclosed here makes it possible to use a draft shield that surrounds the load receiver and is connected to the base frame. This draft shield can be matched to the target containers being used. Accordingly, its interior volume can be kept very small. As the transfer of the dosage-dispensing unit or functional unit from the holder to the target container is in essence a vertical movement, the draft shield preferably is at least partially open in the direction of the upper horizontal plane, i.e. towards the top.

To close off the draft shield also from above during a dosage-dispensing process, a suitable draft shield cover according to a first embodiment can be arranged on the receiving device. This draft shield cover has at least one cutout for an outlet orifice that is formed on the dosage-dispensing unit or the functional unit. In the case of a functional unit, as described previously herein, it can be the working element of the functional unit, for example a temperature sensor or a stirrer, that reaches through the cutout, rather than an outlet orifice.

According to a second embodiment, the draft shield cover can also be arranged on the dosage-dispensing unit or functional unit. This version of the draft shield cover, too, allows the opening from above into the draft shield compartment to be closed off. Of course, the entire draft shield could also be formed as a part of the dispensing head and could completely enclose the target container and the load receiver during the dosage-dispensing process.

If the part of the dosage-dispensing unit that contains the outlet orifice is intended to reach partially into the target container, there needs to be a sufficiently large opening in the draft shield cover. Preferably, the contour of the opening of the draft shield that is partially open from above is matched to the profile of that part of the dosage-dispensing unit which is located in this opening during the dosage-dispensing process.

As a result of the foregoing measures, an exchange of air between the interior space of the draft shield and the ambient environment is largely prevented.

If the substances being dispensed are sticky, it is possible that individual particles remain clinging to the outside of the housing of the dosage-dispensing unit in the area around the outlet orifice. Also, the functional units in particular are contaminated after use. Preferably therefore, a cleaning device is arranged on the base frame for the cleaning of the dosage-dispensing units and functional units. Depending on the design of the dosage-dispensing device, the cleaning device can be arranged near the holder or also in an intermediate position. The arrangement in the area of the holder has the advantage that the holding position can be brought within the range of action of the cleaning device through a sliding movement or a rotation of the holder relative to the base frame. If the cleaning device is arranged in an intermediate position, moving the receiving device to the cleaning device may, as previously mentioned, require additional secondary movements in the horizontal and vertical direction. A cleaning device can be a wiper device and/or a vacuum-suction device and/or a washing station.

Obviously, the holder is not limited to having just one holding position but can have a plurality of holding positions for dosage-dispensing units and functional units arranged side-by-side in a linear array in a horizontal plane. Every holding position is arranged with the capability of linear movement relative to the base frame and to a defined transfer location that occupies a fixed place relative to the base frame. The changing mechanism is configured in such a way that at this transfer location the receiving device receives the currently needed dosage-dispensing unit or functional unit from, and also returns it to, its holding position.

If the holder needs to accommodate a large number of dosage-dispensing units and functional units, it may be practical if the holder has a plurality of holding positions for dosage-dispensing units arranged adjacent to each other in a ring-shaped configuration in a horizontal plane. This holder can turn relative to the base frame about a vertical axis of rotation. Consequently, every holding position can be moved to a defined transfer location which is at a fixed place relative to the base frame.

It is considered self-evident that at least one intermediate holder in at least one intermediate horizontal plane can be arranged between the upper plane of the base frame where the holder is arranged and the lower plane of the base frame where the weighing cell with the load receiver is arranged. To make it possible for dosage-dispensing units and functional units to be transferred from the upper plane to the lower plane, the intermediate holder should have at least one transit position for the receiving device. This transit position can therefore not be occupied by a holding position.

The at least one dosage-dispensing unit can be filled with a substance in the form of a powder, paste or liquid. However, the dosage-dispensing unit can also have a supply conduit which is connected to a reservoir container and possibly to a pump.

In addition, a large number of different functional units can be employed. For example, a functional unit can be a titrator unit, a pump unit, a pipetting unit, a unit with pipe conduits and armatures, a container unit, a sensor unit or an adapter to receive one of the foregoing units, or other units. Such other units that could be employed include for example stirrers, grinders, as well as heating and/or cooling units. As the user can select from a wide diversity of compatible functional units, the dosage-dispensing device is not limited to the dispensing of pulverous or pasty dosage materials as well as liquids, but can be converted into a kind of mini-laboratory for the further treatment of the dosage material, wherein weight values can be continuously registered by way of the force-measuring device.

BRIEF DESCRIPTION OF THE DRAWINGS

Details of the disclosed embodiments of the dosage-dispensing device can be found in the following description of examples of embodiments that are illustrated in the drawings, wherein.

DETAILED DESCRIPTION

Figure 1:
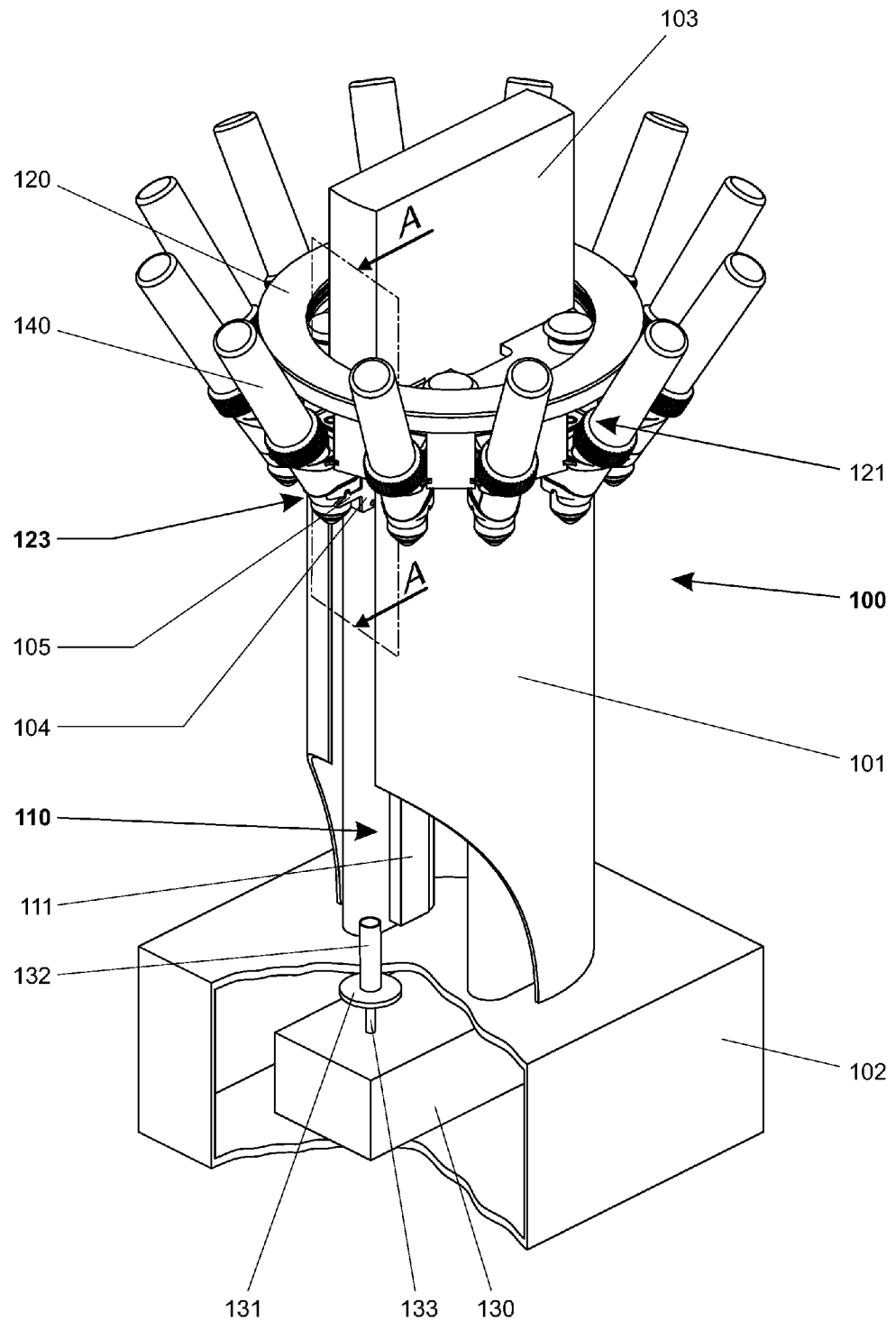
FIG. 1 is a schematic three-dimensional representation of a dosage-dispensing device with a changing mechanism, a base frame, a ring-shaped holder which is rotatably supported on the base frame, a drive mechanism and a receiving device that are connected to the base frame by way of the changing mechanism, further with a weighing cell arranged on the base frame and equipped with a load receiver, and with twelve dosage-dispensing units seated in the holder.

In a schematic three-dimensional representation, FIG. 1 illustrates a dosage-dispensing device 100 with a changing mechanism 110. The dosage-dispensing device 100 has a base frame 101. Arranged on an upper plane of the base frame 101 and connected to the latter is a ring-shaped holder 120 which is supported on the base frame 101 with the ability to turn about a vertical axis of rotation. The holder 120 has a total of twelve holding positions 121, each of which is occupied by a dosage-dispensing unit 140. Of course, it is not necessary that all of the holding positions 121 be occupied for the dosage-dispensing device 100 to function correctly. As a preferred feature, the location of each holding position 121 is stored in an electronic memory unit, so that an operating program which can be executed in a processor module of the dosage-dispensing device 100 can find a desired holding position 121 and turn it to a transfer location 123. Obviously, this memory unit can also be used to store data of the dosage-dispensing unit 140 that has been set into the holding position 121. If an electronic reader device, for example an RFID reader, is arranged in the area of the holder 120, and if the dosage-dispensing unit 140 carries an identifying mark, for example an RFID tag, the registration of the data of each dosage-dispensing unit 140 can also take place automatically at the time of loading the holder 120 with dosage-dispensing units 140. Such data can represent the operating history of the dosage-dispensing unit 140, as for example the date it was first put into operation, the number of dispensing cycles performed, the date of the last previous dispensing cycle, and similar information. Further data can relate to the substance contained in the dosage-dispensing unit 140, for example its identity and composition, its expiration date, measured parameters regarding its flow properties and the like. Obviously, instead of the dosage-dispensing units 140, the holding positions 121 can also be occupied by any of the functional units disclosed in EP 1 959 243 A1. These functional units can likewise carry an RFID memory chip on which technical data are stored concerning the function of the respective functional unit. Possibly, this memory chip may also contain information for the user or even program modules that can be retrieved, which serve to influence and/or control individual process steps of the dosage-dispensing device 100. Particularly for the acquisition of data, the independent mobility of the holder 120 proves to be very advantageous. Thus, the holder 120 can be loaded from a single direction even during a dosage-dispensing process, and only one read/write device is needed to register the data of all RFID storage chips.

On a lower level of the base frame 101, a housing 102 is configured which is shown partially cut away in the drawing in order to expose a weighing cell 130 which is arranged inside the housing 102. A load receiver 131 which, in the operating position of the dosage-dispensing device 100, is arranged above the housing 102 is connected to the weighing cell 130 by means of a force-transmitting member 133 which rises through a passage opening in the housing 102. A target container 132 is resting on the load receiver 131.

Partially visible inside the tubular-shaped base frame 101 is a vertical linear guide 111 of the changing mechanism 110. By means of this vertical linear guide 111, a drive mechanism 103 and a just barely visible receiving device 104 are guided in vertical sliding motion. The driving mechanism 103 is designed to be coupled to a discharge-rate controlling element arranged in the dosage-dispensing unit 140 but not shown in FIG. 1. As soon as it is coupled to the drive mechanism 103 and actuated by it, the discharge-rate controlling element opens up an outlet orifice of the dosage-dispensing unit 140. With the passage through the outlet orifice set free, the dosage material stored in the dosage-dispensing unit 140 can now flow into a target container 132 arranged below the outlet orifice.

Figure 6:
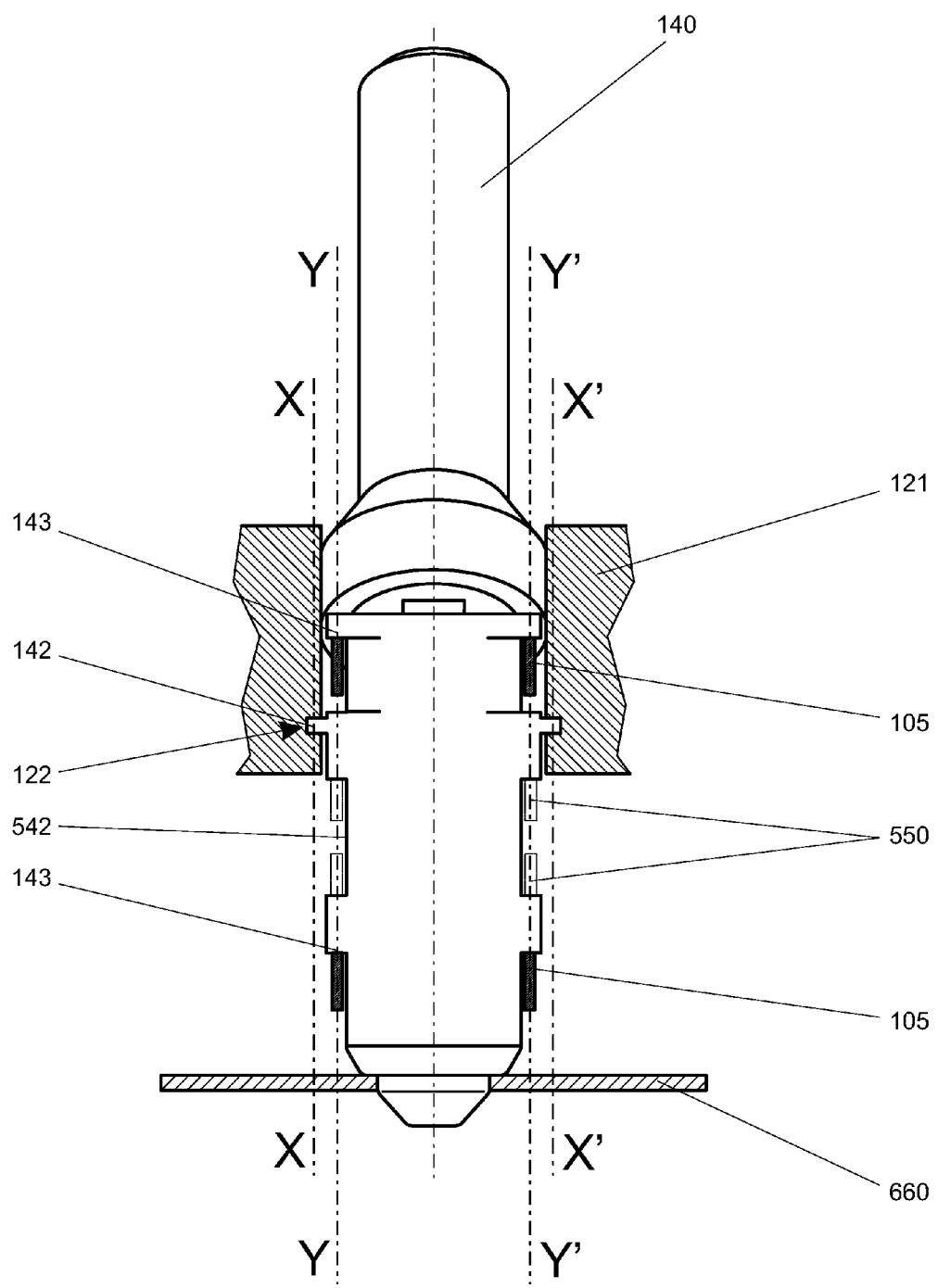
FIG. 6 shows a dosage-dispensing unit seated in the holding position of a holder, as an elevation drawing in the plane A-A which is defined in FIG. 1.

The holding position 121 which is currently at the transfer location 123 is occupied by a dosage-dispensing unit 140. FIG. 1 illustrates a point in time where the changing mechanism 110 is ready for the transfer of a dosage-dispensing unit 140 to the receiving device 104, as the support 105 of the receiving device 104 is engaging the dosage-dispensing unit. The detailed design of the receiving device 104 and the changing mechanism 110 will be covered more extensively in the following description of FIG. 2. The arrangement of the guide tracks, seating locations, supports and holder grooves which cooperate in a smooth transfer will be described later herein in the context of FIG. 6, representing the view in the plane A-A which is outlined and identified in FIG. 1.

Figure 2:
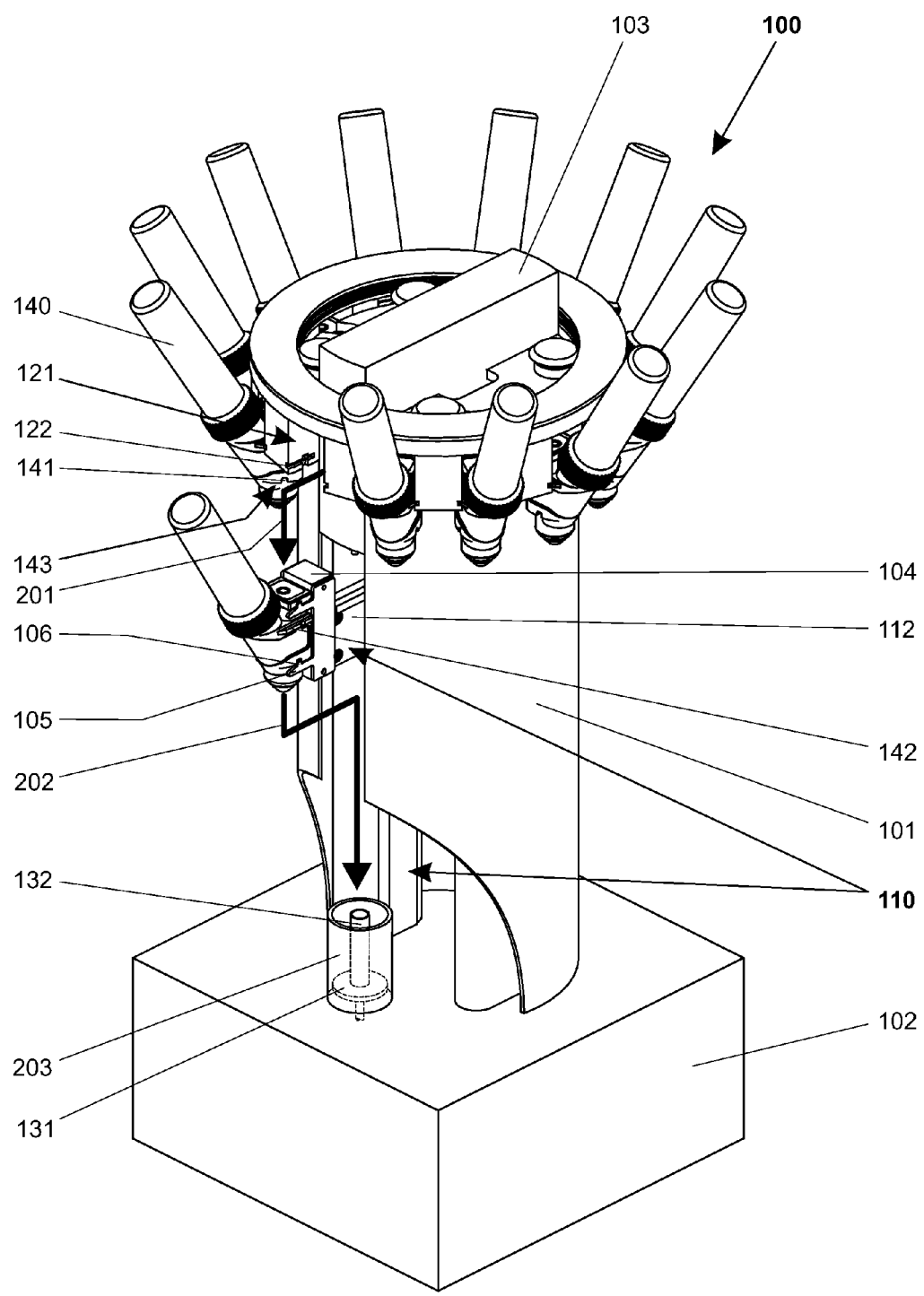
FIG. 2 shows the FIG. 1 dosage-dispensing device in schematic three-dimensional representation, wherein the load receiver and a target container set on the load receiver are enclosed by a draft shield, and wherein the receiving device and the dosage-dispensing unit seated in it are at an intermediate position between the holder and the weighing cell.

FIG. 2 again shows the dosage-dispensing device 100 of FIG. 1. All elements that have already been described in FIG. 1 carry the same reference symbols. FIG. 2 gives a clearer impression of the changing mechanism 110 with its two linear guides 111, 112. The horizontal linear guide 112 of the changing mechanism 112 is arranged between the drive mechanism 103 and the receiving device 104. Thus, the receiving device 104 can slide horizontally relative to the driving mechanism 103 and the base frame 101. The drive mechanism 103, the horizontal linear guide 112 and the receiving device 104 are restricted to joint vertical movement relative to the base frame 101 by the vertical linear guide 111. Furthermore, each of the linear guides 111, 112 has its own drive mechanism (not shown in the drawing) which can operate under the command of a controller (likewise not shown). The controller can be part of the changing device 110. However, it may be more advantageous if the drive mechanisms are controlled directly by the controller of the dosage-dispensing device 100 or by a controller system that is independent of the dosage-dispensing device 100.

The receiving device 104 is configured in the shape of a fork and has four supports 105 extending in the horizontal direction, each support 105 having a vertically directed projection 106. When the dosage-dispensing unit 140 is seated in the receiving device 104, the supports 105 are engaged in seating locations 143 which are formed on the dosage-dispensing unit 140. Only two of the supports 105 are visible as the view of the other two is blocked by the installed dosage-dispensing unit 140. The projections 106 are engaged in recesses 141 which are formed on the dosage-dispensing unit 140 and thereby prevent the dosage-dispensing unit 140 from falling out of the receiving device 104 during transport by means of the changing mechanism 110. Seating a dosage-dispensing unit 140 in the receiving device 104 as well as removing the dosage-dispensing unit 140 from the receiving device 104 therefore requires a short vertical movement of the receiving device 104 relative to the dosage-dispensing unit 140.

In the time phase illustrated in FIG. 2, the transfer of the dosage-dispensing unit which was described in FIG. 1 has already been completed, and the dosage-dispensing unit 140 is shown here on its way to the target container 132, with the first arrow 201 indicating the path already traveled and the second arrow 202 indicating the travel path still left to be completed. The first arrow 201 has a horizontal section and a vertical section. The horizontal section indicates that the dosage-dispensing unit 140 has been moved out of the holding position 121 in a horizontal movement directed away from the base frame 101. This is possible only if the guide tracks 142 formed on the dosage-dispensing unit 140 and the corresponding holder grooves 122 of the holding position 121 extend parallel to the horizontal section of the first arrow 201. As soon as the dosage-dispensing unit is completely free of the holding position, the vertical movement can be started. The second arrow 202 likewise has a horizontal section, indicating a horizontal movement of the dosage-dispensing device 140 directed towards the drive mechanism 103 up to the point where the dosage-dispensing unit 140, more specifically its discharge-rate controlling element, can be coupled to the drive mechanism 103. Also with this movement, the dosage-dispensing unit 140, in particular its outlet orifice, is brought into alignment with the fill opening of the target container 132. To protect the target container 132 and the load receiver 131 from turbulent air movements which could affect the weighing signal, a draft shield 203 which is open at the top is installed on the housing 102.

Figure 3:
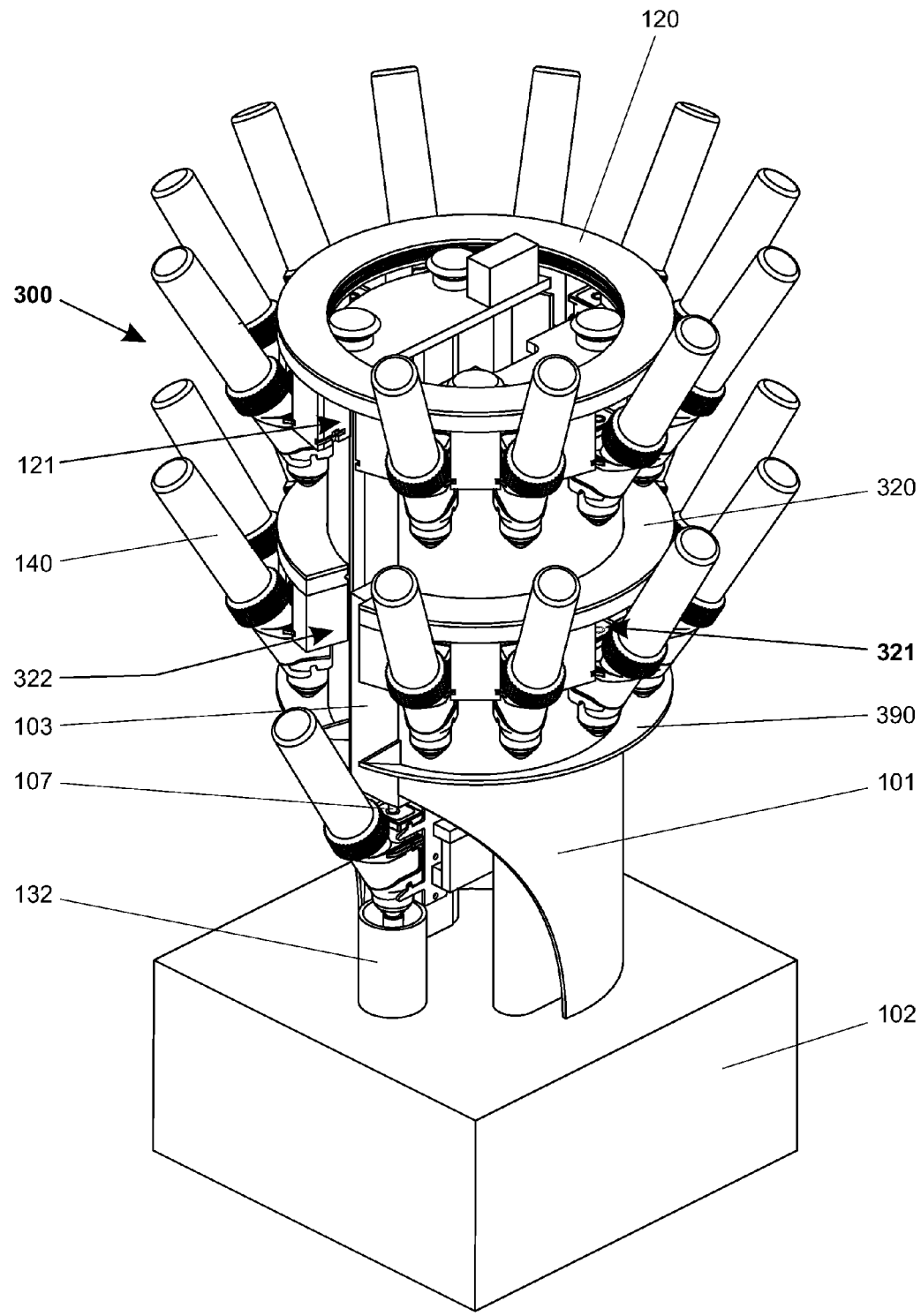
FIG. 3 shows in essence the schematic three-dimensional illustration of the FIG. 1 dosage-dispensing device with the addition of an intermediate holder which is arranged on the base frame between the holder and the target container, and wherein the receiving device and the dosage-dispensing unit that is seated in it are positioned immediately above the target container.

The dosage-dispensing device 300 shown schematically in FIG. 3 is essentially the same as represented in FIGS. 1 and 2. Identical elements that have already been described in FIGS. 1 and 2 are again identified by the same reference symbols. In essence, the dosage-dispensing device 300 is distinguished from the previously described FIGS. 1 and 2 by an intermediate holder 320 which is arranged in an intermediate horizontal plane between the holder 120 and the housing 102. Like the holder 120, the intermediate holder 320 is pivotally connected to the base frame 101 with the ability to turn about a vertical axis of rotation. The intermediate holder 320 with its holding positions 321 is configured almost identical to the holder 120, the difference being essentially that a transit position 322 takes the place of one of the holding positions 321. This is necessary in order to allow dosage-dispensing units 140 to be moved from the holder 120 to the target container 132.

FIG. 3 shows the dosage-dispensing device 300 during a dosage-dispensing process. The drive mechanism 103, the receiving device 104 and the dosage-dispensing unit 140 seated in the receiving device 104 are located on the lower plane of the base frame 101, closely above the fill opening of the target container 132. The discharge-rate controlling element of the dosage-dispensing unit 140 is coupled to a drive shaft 107 of the drive mechanism 103. As soon as the drive shaft 107 actuates the discharge-rate controlling element, the outlet orifice of the dosage-dispensing unit 140 is set free, and dosage material is discharged from the dosage-dispensing unit 140 into the target container 132. After the dosage-dispensing process is completed, the dosage-dispensing unit 140 is returned to its assigned holding position 121, 321 along the same path as indicated in FIG. 2 by the arrows 201, 202, but obviously in the reverse direction.

Also indicated schematically in FIG. 3 is a collecting tray 390 which is arranged on the base frame 101 below the intermediate holder 320. The collecting tray 390 is ring-shaped and serves to collect dirt, for example substance particles that can be present in the vicinity of the outlet orifice of the dosage-dispensing units 140. Obviously, the design of the collecting tray 390 could be further developed, for example by adding a slidable segment in order to also cover the transit position 322. Also, a closed housing could be added to the collecting tray 390, so that the dosage-dispensing units 140 seated at the holding positions 121, 321 are completely enclosed inside this housing. Naturally, the interior space of such a housing could be flooded continuously with a protective gas in order to protect the substances in the dosage-dispensing units 140 from being affected by the ambient atmosphere.

Figure 4:
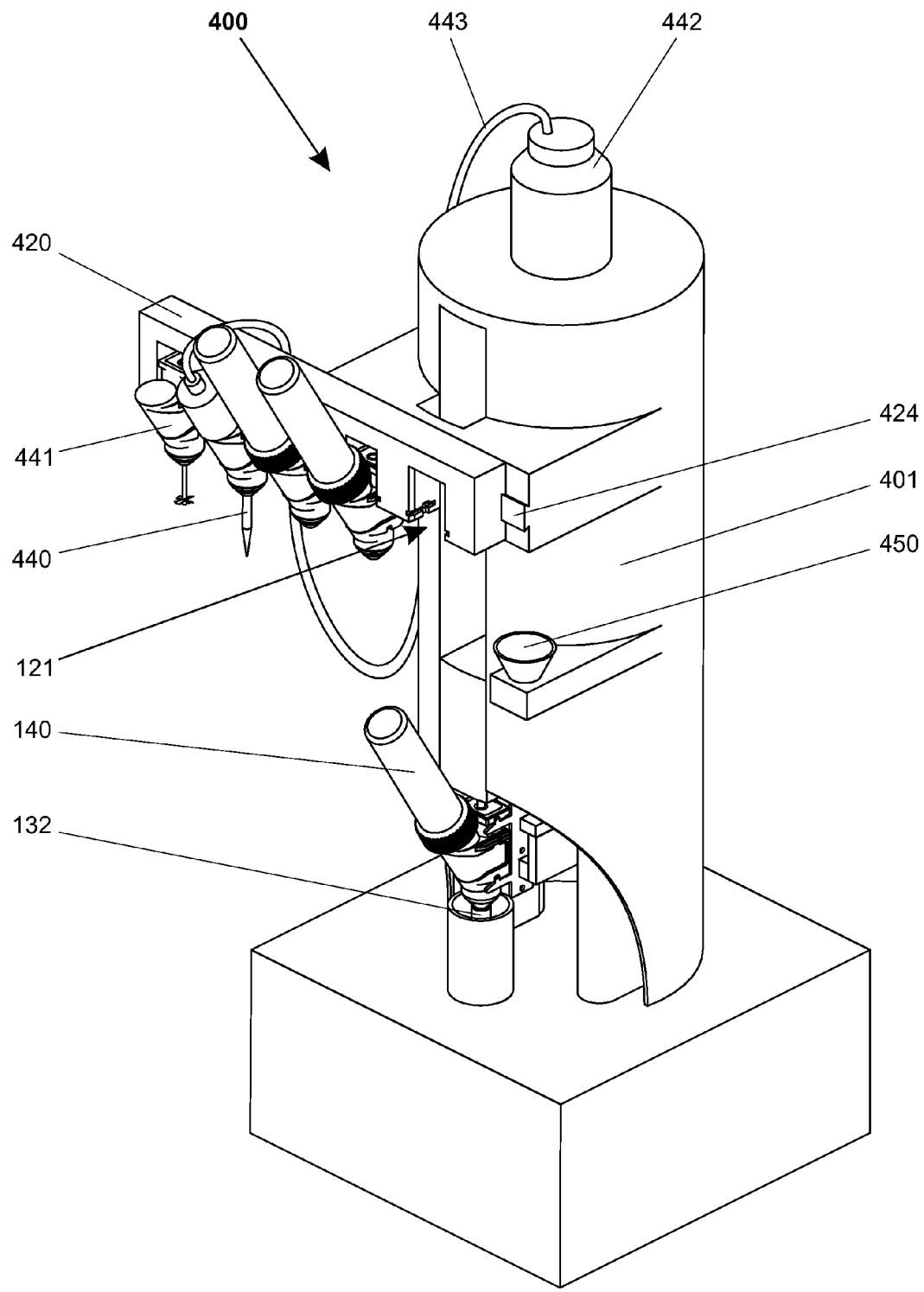
FIG. 4 is a schematic three-dimensional representation of a dosage-dispensing device with a changing mechanism, a base frame, a holder which is supported on the base frame with the mobility to slide in a straight line, a drive mechanism and a receiving device that are connected to the base frame by way of the changing device, further with a weighing cell arranged on the base frame and equipped with a load receiver, and with three dosage-dispensing units and two functional units seated in the holder.

FIG. 4 shows a schematic three-dimensional representation of a dosage-dispensing device 400. All elements that were described already in FIGS. 1 to 3 keep the same reference symbols. The base frame 401 differs slightly from the base frame in the preceding examples. This is due to the fact that the dosage-dispensing device 400 has a holder 420 which is constrained by means of a longitudinal guide track 424 to move in a straight horizontal line. The holding positions 121 which are formed on the holder 420 are analogous in their configuration to the holding positions described previously. The dosage-dispensing device 400 is occupied by three dosage-dispensing units 140 and two functional units 440, 441. The first functional unit 440 is a pump unit which serves to pump a liquid from a separate reservoir container 442 through a supply conduit into the target container 132. If the interior of the reservoir container 442 is pressurized with a gas, the functional unit 440 can also be equipped only with a micro valve, as the liquid is propelled by the gas pressure to move from the reservoir container towards the micro valve. The second functional unit is a stirrer which can be used, for example, to stir a powder dispensed from the dosage-dispensing units 140 into the liquid which is added through the pump unit.

After the stirring activity, the stirrer is wetted and thus contaminated by the solution that is present in the target container 132. As a means to clean the functional units 440, 441 and dosage-dispensing units 140, the dosage-dispensing device 400 can be equipped with a cleaning device 450, represented here only in schematic outline, which can be arranged on the base frame 401. The cleaning can take place for example in such a way that after the functional unit 440, 441 has been in use, it is first transported to its holding position 121 and the latter is then moved to the cleaning device 450. However, arrangements are also possible where a dosage-dispensing unit 140 or functional unit 440, 441 passes through the cleaning device 450 during the return to the holding position 121. The cleaning device 450 can of course include different accessory modules, for example a vacuum suction device for dosage-dispensing units 140 that are contaminated by a powder, and/or a washing station for contaminated functional units 440, 441. In addition, other elements may be used such as brushes, hot-air blow-dryers and the like.

Figure 5A:
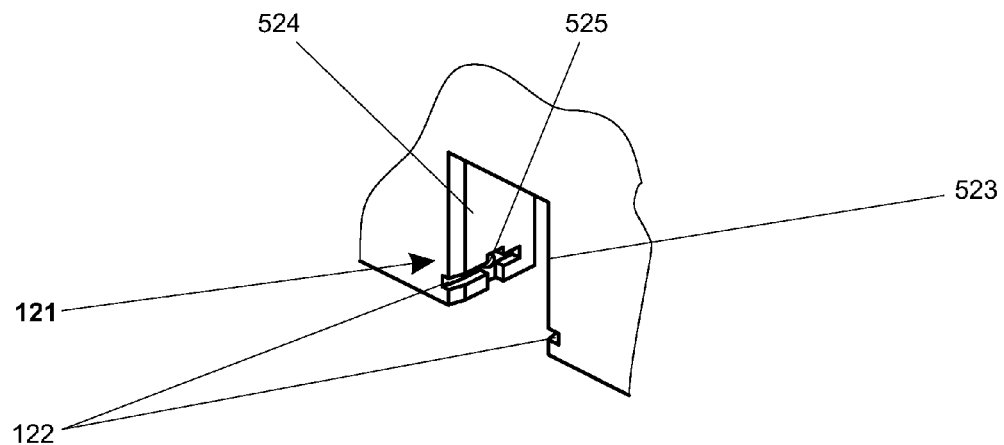
FIG. 5A shows a three-dimensional detail view of a holding position belonging to the holder of FIGS. 1 to 3.

To better illustrate and describe certain details, FIG. 5A shows a three-dimensional detail view of one of the holding positions 121 which are present, preferably in plural arrangements, in the holders of the preceding FIGS. 1 to 4. Each holding position 121 is formed in essence by a U-shaped cutout in the holder, with the open part of the U facing downward. The cutout has two side walls 523, 524, each of which has a holder groove 122. At least one of the holder grooves has a snap-lock element 525. The snap-lock element 525 in FIG. 5A, which is only partially visible, is a spring-biased ball catch of conventional design consisting essentially of a ball and a compressive spring which are arranged in a blind hole (the spring being behind the ball and therefore not visible).

Figure 5B:
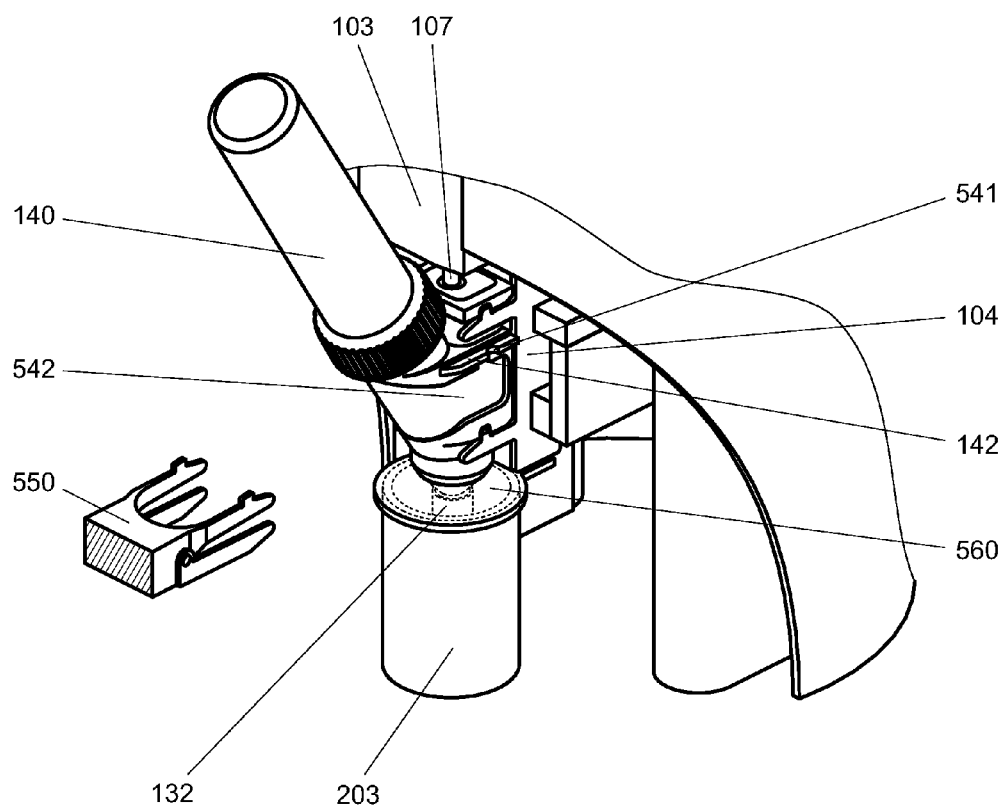
FIG. 5B shows a three-dimensional detail view of the dispensing head of FIGS. 3 and 4 positioned above the target container, with the addition of a draft shield cover which is arranged on the receiving device, and further with a part of a gripper of a loading mechanism being indicated in the drawing.

FIG. 5B represents a three-dimensional view of a detail of FIGS. 3 and 4, wherein a dosage-dispensing unit 140 is shown seated in the receiving device 104. The dosage-dispensing unit 140 is positioned above the target container 132, i.e. in operating position for a dispensing cycle. As can further be seen in the drawing, the drive mechanism 103 is coupled to the dosage-dispensing unit 140 through the drive shaft 107. Consequently, the drive mechanism 103 is operable to actuate a discharge valve of the dosage-dispensing unit 140.

As has already been mentioned in the description of FIG. 2, there is a guide track 142 formed on the dosage-dispensing unit 140. The guide track 142 further has an indent 541 which, when the dosage-dispensing unit 140 is seated in the holding position 121, is engaged by the snap-lock element 525 described in FIG. 5A. This is necessary because when the dosage-dispensing unit 140 or functional unit 440, 441 is inserted into the holding position 121 it simultaneously needs to be extracted from the receiving device 104, and overcoming the friction will take a certain amount of force. Also, the snap-lock element 525 secures the dosage-dispensing unit 140 against accidentally falling out of the holding position 121.

FIG. 5B further shows a draft shield cover 560 which is attached to the receiving device 104. A part of the dosage-dispensing device 140 reaches through an opening in the draft shield cover 560, wherein the contour of the opening in the draft shield cover is matched to the profile of said part in such a way that the opening is almost completely closed off when a dosage unit 140 is seated in the receiving device 104. When the dosage-dispensing unit is in position to perform a dispensing cycle, the draft shield cover 560 lies snug against the draft shield 203. To prevent the draft shield cover 560 and/or the draft shield 203 from getting damaged as a result of the vertical movements of the changing device, the dosage-dispensing device can be equipped with a suitable sensor which sends a signal to the controller of the changing device as soon as the draft shield 203 and the draft shield cover 560 make contact with each other.

If the dosage-dispensing device is incorporated in a larger system, it may be practical to use a loading mechanism (part of which is shown in FIG. 5B) to fill the holding position 121 and the entire holder. This purpose is served by at least one coupling area 542 that is formed on the dosage-dispensing unit 140 or the functional unit 440, 441 for the engagement of a robotic gripper. The loading mechanism, for example an industrial robot, has a gripper 550 which can connect to the coupling area 542, so that the dosage-dispensing unit 140 or functional unit 440, 441 can be connected to the loading mechanism through a contact-force engagement and/or a form-fitting engagement. Preferred is a setup where the loading mechanism is independent of the dosage-dispensing device. It is practical if the loading of the holding position 121 with a dosage-dispensing unit 140 or functional unit 440, 441 is performed by means of a horizontal movement that is directed towards the base frame, since no components of the dosage-dispensing device obstruct a movement in this direction. Of course, the holding position 121 and specifically the holder grooves 122 need to be configured in such a way that the loading from this direction, from "in front" so to speak, is possible.

FIG. 6 represents an elevation drawing in the plane A-A which is defined in FIG. 1, showing a dosage-dispensing unit 140 seated in the holding position 121 of a holder. In the interest of a particularly compact configuration of the dosage-dispensing unit 140 or functional unit, of the holding position 121, and of the receiving device, a design suggests itself where the supports 105 of the receiving device can reach into the holding position 121. This is possible if the dosage-dispensing unit 140 or functional unit is arranged between a vertically oriented inner pair of planes Y, Y' and an outer pair of planes X, X'. Each plane of the inner pair of planes Y, Y' contains for example two seating locations 143, one located above the other, as well as a coupling area 542 for a gripper. Each plane of the outer pair of planes X, X' contains a guide track. The receiving device and the holding locations 121 are designed accordingly, wherein each of the holder grooves 122 is arranged in a plane of the outer pair of planes X, X'. Two supports 105 of the receiving device, one above the other, are arranged in each plane of the inner pair of planes Y, Y'. In addition, the gripper 550 is matched to the coupling area 542 which is arranged in the inner planes. As a variation of FIG. 5B, the draft shield cover 660 in FIG. 6 is coupled to the dosage-dispensing unit 140 rather than to the receiving device. Obviously, the draft shield 203 can also be attached to the draft shield cover 560 of the receiving device 104, or to the draft shield cover 660 of the dosage-dispensing unit 140, instead of being attached to the housing 102.

While the invention has been described through the presentation of specific examples of embodiments, it is evident that numerous other variations of embodiments could be created once the present invention is known, for example by combining a feature such as the draft shield cover of an individual embodiment with another embodiment, and/or by interchanging individual functional units between different embodiments. In particular the arrangement of the supports, of the seating locations, the guide grooves and the guide tracks on the inner and outer pairs of planes is subject to professional preference. It is possible to develop this concept into a differentiating code, so that functional units and dosage-dispensing units can be inserted into different, exclusively reserved holding locations. It is further conceivable that several receiving devices and several drive mechanisms are arranged on one changing device. The dosage-dispensing device can also have several changing devices that are operable independently of each other, each with a receiving device and a driving mechanism. Accordingly, such combinations and alternatives are considered to be included in the invention.

What is claimed is:

1. A device for dispensing a dosage into a target container having a fill opening, the device comprising:
   a base frame;
   at least two selectable units, a first of which is a unit for dispensing a dosage with the second and any further units selected from a group consisting of units for dispensing dosages and units for performing function;
   at least one receiving device, each receiving device adapted for insertion of a selected one of the selectable units therein; and
   a holder, arranged on an upper horizontal plane of the base frame when the device for dispensing a dosage is in an operating position, the holder comprising a plurality of holding positions, arranged horizontally and side-by-side, each of which is adapted for holding a selected one of the selectable units;
   at least one drive mechanism, arranged for coupling to one of the selectable units that is inserted into the receiving device;
   a weighing cell arranged on a lower horizontal plane of the base frame, the weighing cell having a load receiver adapted to receive the target container; and
   a changing mechanism that moves the receiving device horizontally relative to the base frame to a transfer location, so that a selected one of the selectable units can be exchanged between a designated one of the holding positions in which it is inserted and the receiving device, or vice versa, the changing mechanism operating to move the receiving device, along with the drive mechanism, vertically relative to the base frame, both towards the fill opening of the target container that has been set on the load receiver and away from the fill opening towards the designated holding position.

2. The device of claim 1, further comprising:
   at least two holder grooves in one of the plurality of holding positions; and
   at least two supports in the receiving device, and
   guide tracks and seating locations, formed on each of the selectable units, the guide tracks corresponding to the holder grooves and the seating locations corresponding to the supports.

3. The device of claim 2, wherein:
   each of the selectable units is arranged between a pair of vertically oriented inner planes along which at least one seating location is located and a pair of vertically oriented outer planes along which at least one guide track is located.

4. The device of claim 2, further comprising:
   a location, formed on each of the selectable units, for coupling connection thereof with a robotic gripper of a loading mechanism that is independent of the device for dispensing a dosage.

5. The device of claim 2, further comprising:
   a snap-lock element, releasable by a mechanical force, arranged between at least one of: one of the holder grooves and the corresponding guide track and one of the supports and the corresponding seating location.

6. The device of claim 2, further comprising:
   a recess, located in one of the holder grooves or in one of the seating locations, extending in the vertical direction and orthogonal to a longitudinal axis of the holder groove or seating location; and
   a projection, formed on the corresponding guide track or on the corresponding support, extending essentially in the vertical direction and orthogonal to a longitudinal axis of the guide track or the support,
   such that vertical set-down and unlocking movements are required to respectively, set or separate one of the selectable units from the corresponding receiving device or holding position.

7. The device of claim 1, further comprising:
   a draft shield that surrounds the load receiver, and is at least partially open in the direction towards the upper horizontal plane of the base frame.

8. The device of claim 7, further comprising:
   a draft shield cover, arranged on the receiving device such that an open top of the draft shield can be closed off, the draft shield cover comprising a cutout for an outlet formed on a selectable unit inserted in the receiving device.

9. The device of claim 7, further comprising:
   a draft shield cover, arranged on the dosage-dispensing unit or functional unit to close off an open top of the draft shield.

10. The device of claim 7, wherein:
    the draft shield has a contour at the partially open top thereof that corresponds to to a profile of a part of the selectable unit which is located therein during a dosage-dispensing process.

11. The device of claim 1, further comprising:
    a device for cleaning a selected one of the selectable units, arranged on the base frame.

12. The device of claim 1, wherein:
    the holding positions are arranged in a linear array in a horizontal plane, with each holding position arranged for linear horizontal translation relative to the base frame to the transfer location, which is fixed relative to the base frame.

13. The device of claim 12, further comprising:
a further holder, arranged in a horizontal plane between the respective upper and lower horizontal planes, the further holder comprising a transit position for the receiving device.

14. The device claim 13, wherein:
each of the holder and the further holder are arranged to shift sideways when the receiving device is in the area of the lower plane.

15. The device of claim 1, wherein:
the holding positions are arranged in a ring-shaped adjacent configuration in a horizontal plane, with each holding position arranged for rotary horizontal translation about a vertical axis to the transfer location, which is fixed relative to the base frame.

16. The device of claim 15, further comprising:
a further holder, arranged in a horizontal plane between the respective upper and lower horizontal planes, the further holder comprising a transit position for the receiving device.

17. The device claim 16, wherein:
each of the holder and the further holder are arranged to rotate about the vertical axis when the receiving device is in the area of the lower plane.

18. The device of claim 1, wherein:
each of the units for dispensing a dosage either contains a substance in the form of a powder, paste or liquid or has a supply conduit which is connected to a reservoir container of the substance.

19. The device of claim 18, wherein:
at least one of dosage-dispensing units has a supply conduit which is connected to a pump.

20. The device of claim 1, wherein:
the units for performing functions are selected from a group consisting of: a titrator unit, a pump unit, a pipetting unit, a unit with pipe conduits and armatures, a unit with a stirrer device, a sensor unit, a heating- and/or cooling unit, and an adapter to receive one of the units or other units.

21. A device for dispensing a dosage of a plurality of substances, in the form of a powder, paste or liquid, into a target container having a fill opening, the device comprising:
a base frame;
a plurality of units for dispensing the dosages, each unit corresponding to one of the substances;
at least one receiving device, each receiving device adapted for insertion of a selected one of the units for dispensing the dosages therein; and
a holder, arranged on an upper horizontal plane of the base frame when the device for dispensing a dosage is in an operating position, the holder comprising a plurality of holding positions, arranged horizontally and side-by-side, each of which is adapted for holding a selected one of the units for dispensing the dosages;
at least one drive mechanism, arranged for coupling to one of the units for dispensing the dosages that is inserted into the receiving device;
a weighing cell arranged on a lower horizontal plane of the base frame, the weighing cell having a load receiver adapted to receive the target container; and
a changing mechanism that moves the receiving device horizontally relative to the base frame to a transfer location, so that a selected one of the units for dispensing the dosages can be exchanged between a designated one of the holding positions in which it is inserted and the receiving device, or vice versa, the changing mechanism operating to move the receiving device, along with the drive mechanism, vertically relative to the base frame, both towards and away from the fill opening of the target container that has been set on the load receiver.

* * * * *